United States Patent [19]

Béres et al.

[11] Patent Number: 5,707,654
[45] Date of Patent: Jan. 13, 1998

[54] SUGAR- AND SODIUM-FREE EFFERVESCENT TABLETS AND GRANULES AND PROCESS FOR PREPARING SAME

[75] Inventors: József Béres, Kisvárda; József Béres; László Lex, both of Budapest; Istvánné Bárkányi, Tiszavasvári, all of Hungary

[73] Assignee: Beres Reszvenytarsasag, Budapest, Hungary

[21] Appl. No.: 513,973

[22] PCT Filed: Mar. 10, 1994

[86] PCT No.: PCT/HU94/00006

§ 371 Date: Sep. 7, 1995

§ 102(e) Date: Sep. 7, 1995

[87] PCT Pub. No.: WO94/20077

PCT Pub. Date: Sep. 15, 1994

[30] Foreign Application Priority Data

Mar. 10, 1993 [HU] Hungary .............. P 93 00680

[51] Int. Cl.$^6$ .................. A61K 9/16; A61K 9/46

[52] U.S. Cl. .................. 424/466; 424/489
[58] Field of Search .................. 424/466, 489

[56] References Cited

U.S. PATENT DOCUMENTS 5,424,074  6/1995  Koli et al. .................. 424/464

Primary Examiner—Thurman K. Page
Assistant Examiner—James M. Spear
Attorney, Agent, or Firm—Keil & Weinkauf

[57] ABSTRACT

The invention relates to effervescent tablets and granules comprising a shell material, a basic sparkling component, an acidic sparkling component, and a sweetening agent, macro- and microelements and vitamins as active agents. The effervescent tablets and granules comprise 20–50% by mass of mannitol as shell material, 8–25% by mass of potassium hydrogen carbonate as basic sparkling component, 9–27% by mass of malic acid as acidic sparkling component, and 0.4–2.2% by mass of aspartame as sweetening agent. Furthermore, the invention relates to a process for preparing the above-described effervescent tablets and granules.

6 Claims, No Drawings

5,707,654

SUGAR- AND SODIUM-FREE EFFERVESCENT TABLETS AND GRANULES AND PROCESS FOR PREPARING SAME

This application is a 371 of PCT/HU94/00006 filed Mar. 10, 1994.

The invention relates to sugar- and sodium-free effervescent tablets and granules and a process for their preparation.

More specifically, the invention relates to effervescent tablets and granules comprising a shell material, a basic effervescent and disintegrating (further on: sparkling) component, an acidic sparkling component, and a sweetening agent, further macro- and trace elements and optionally vitamins. Furthermore, the invention relates to a process for the preparation of such tablets and granules.

It is known that nowadays one of the most popular pharmaceutical form for introducing medicines, vitamins and mineral substances to the organism is the so-called effervescent tablet (Pharmaceutical Dosage Form: Tablets, Vol. I., 2nd edition, A. Lieberman ed., 1989, Marcel Dekker, Inc.). The development of this form is supported from the viewpoint of pharmaceutical effect, beside commercial reasons, by several factors, e.g. the decrease of stomach irritation, the enhancement of absorption, etc. The solution of such tablets in water results in a carbonated or sparkling beverage containing carbon dioxide.

The spectacular disintegration of effervescent tablets is caused by a mixture consisting of an acid and a base, wherein said mixture when contacting with water nearly wedges the tablet during evolution of carbon dioxide.

The manufacturing and packaging of effervescent tablets requires high care; consequently, in the practice the direct compressing method is preferred to the wet processes.

Most effervescent tablets comprise three main components beside the active agents: a shell and binding agent, an acidic sparkling agent and a basic sparkling agent.

As shell and binding agent sugars (lactose, saccharose, glucose), sorbitol, xylitol or starch, as acidic sparkling agent citric acid, tartaric acid, fumaric acid or adipic acid while as basic sparkling component sodium hydrogen carbonate, sodium carbonate and magnesium carbonate are generally used.

From the other components generally used in effervescent tablets the following preferable agents are mentioned: sweetening agents such as sugars, saccharin, sodium cyclamate and aspartame; flavouring and aroma agents; lubricating agents such as polyethylene glycols, silicone oils, stearates and adipic acid.

The U.S. Pat. No. 4,725,427 describes an effervescent tablet which contains lactose as shell material, citric acid as acidic sparkling agent, a mixture of sodium hydrogen carbonate and potassium hydrogen carbonate as basic sparkling component and aspartame as sweetening agent. Beside water and fat-soluble vitamins this tablet contains inorganic substances as active agents and these substances are rendered more utilizable biologically by using them in chelate form. This composition does not render possible, however, the preparation of sodium-free tablets and this is a considerable disadvantage since it is well-known that the introduction of an excess of sodium into the organism results in several deleterious physiological effects. A further disadvantage of this composition is caused by the presence of citric acid in an amount of 20–45% by mass since the high amount of this acid may result in harmful physiological effects.

The U.S. Pat. No. 4,678,661 describes effervescent tablets containing a mixture of calcium carbonate and potassium carbonate as basic sparkling component. It is a considerable disadvantage of this tablet that the disagreeable soapy flavour of potassium hydrogen carbonate can be tasted in it. Besides, the use of calcium carbonate unfavourably influences the dissolution time.

The U.S. Pat. No. 4,704,269 describes an effervescent tablet comprising potassium hydrogen carbonate as basic sparkling component, malic acid and citric acid as acidic sparkling components, a mixture of sorbitol and maltodextrin as shell and binding agents and calcium saccharate as sweetening agent. This composition is used as antacid and analgesic; its disadvantage is that, owing to the presence of sorbitol, its storability is not satisfactory. Besides, the sorbitol is not recommended for general use in soft drinks since some individuals have a low gastric tolerance for it (Martindale: The Extra Pharmacopoeia, 19th ed., London, 1989, p. 1274).

The invention aims at preparing effervescent tablets and granules which are chemically stable, can readily be compressed, have advantageous physical properties, are free from sodium and sugar, and contain macro- and trace elements and optionally vitamins in a homogeneous distribution.

The invention is based on the recognition that the above aim can be completely attained if the following components are used as basic materials for preparing effervescent tablets and granules: mannitol as shell material, malic acid as acidic sparkling component, potassium hydrogen carbonate as basic sparkling component and aspartame as sweetening agent.

The invention is further based on the recognition that the use of mannitol renders possible the introduction of salts of macro- and trace elements of high crystal-water content into the composition. Consequently, the invention is based on the overcoming of a technical prejudice since until now it was known that no effervescent tablets and granules can be prepared from such materials due to the fact that the high water content inhibits the compressing and at the same time it results in the premature deliquesce of the tablets.

A further basis of the invention is the recognition that in case of using mannitol for preparing tablets or granules the macro- and trace elements form complexes with the mannitol whereby the incompatibilities of the components can be eliminated during the technological processes, the end-product will be chemically stable, and the mannitol complexes obtained can be more readily absorbed by the organism, that is, they become better utilizable.

A further basis of the invention is the recognition that, in the case of the colon use of mannitol, malic acid and aspartame, the potassium hydrogen carbonate can be used even alone as basic sparkling component whereby it is possible to eliminate the sodium ions from the composition. Besides, with such a combination the unagreeable flavour and the sensitivity to moisture of potassium hydrogen carbonate can be eliminated. Furthermore, in the case of this composition the bad compressibility of potassium hydrogen carbonate, i.e. the property that it strongly adheres to the surface of stamps and matrices which renders impossible its compressing in spaces containing a relative moisture content of 45% or more, can be eliminated. Consequently, the invention is based even in this respect on the overcoming of a technical prejudice. This statement is proved by the fact that the U.S. Pat. No. 4,678,661 contains in column 1, lines 27–32 the following statement: "The utilization of potassium bicarbonate and potassium carbonate alone fails to meet the need because, first, the potassium compounds give the substance an unpleasant soapy taste, and second, the moisture sensitivity due to the introduction of potassium salts leads to great technical problems."

A further basis of the invention is the recognition that in case of the common use of malic acid as acidic sparkling component with mannitol a suitably compressible composition is obtained. This recognition is surprising since it is known that the malic acid alone can not be readily compressed and due to its low melting point it is a technologically difficultly treatable compound which melts while grinding. On the other hand, the use of malic acid in a relatively high amount is rendered possible by our recognition and at the same time the antioxidant and flavour-improving effect of malic acid as well as its ability to optimally setting the pH value can be utilized.

Finally, the invention is based on the recognition that by the common use of mannitol, potassium hydrogen carbonate, malic acid and aspartame it is rendered possible to prepare a composition of low energy content which does not cause gastrointestinal complaints. The tablets prepared from this composition have very high breaking strength and result in a quickly sparkling and clear solution although the composition comprises incompatible vitamins, macro- and trace elements and components (potassium hydrogen carbonate, malic acid, salts of macro- and trace elements of high crystal-water content) having per se bad compressing properties.

Based on the above the invention relates to effervescent tablets and granules comprising a shell material, a basic sparkling component, an acidic sparkling component, and a sweetening agent, furthermore macro- and microelements and optionally vitamins as active agents. According to the invention the effervescent tablets and granules comprise 20–50% by mass, preferably 30–40% by mass, of mannitol as shell material, 8–25% by mass, preferably 14–18% by mass, of potassium hydrogen carbonate as basic sparkling component, 9–27% by mass, preferably 15–21% by mass, of malic acid as acidic sparkling component, and 0.4–2.2% by mass, preferably 0.6–1.5% by mass, of aspartame as sweetening agent, furthermore, if desired, flavouring, lubricating and other additives generally used in the manufacture of effervescent tablets in an amount necessary to supplement the mass of the components to 100%.

Furthermore, the invention relates to a process for preparing effervescent tablets or granules. According to the invention one proceeds by homogenizing 20–50% by mass, preferably 30–40% by mass, of mannitol, 8–25% by mass, preferably 14–18% by mass, of potassium hydrogen carbonate, 9–24% by mass, preferably 15–21% by mass, of malic acid, and 0.4–2.2% by mass, preferably 0.6–1.5% by mass, of aspartame together with the macro- and trace elements and vitamins to be introduced and optionally together with flavouring, lubricating and other additives generally used in the manufacture of effervescent tablets, then granulating the thus-obtained homogenizate to granules ready for compressing, and finally compressing tablets or granules of the desired size and strength.

The effervescent tablets and granules according to the invention contain as macro- and trace elements preferably magnesium, zinc, iron(II), copper(II), manganese(II), and chromium(III) cations, further molybdenum(VI) and selenium(IV) anions.

The iron ions are preferably used in the composition in the form of iron(II)-sulphate heptahydrate, the zinc ions in the form of zinc sulphate heptahydrate, the copper ions in the form of copper sulphate pentahydrate, the manganese ions in the form of manganese sulphate monohydrate, the molybdenum ions in the form of ammonium heptamolybdenate tetrahydrate, the selenium ions in the form of selenious acid, the magnesium ions in the form of magnesium sulphate heptahydrate, and the chromium ions in the form of chromium(III) chloride hexahydrate.

The vitamins are added to the composition preferably in the following amounts: 0.01–0.5% by mass of vitamin $B_1$, 0.01–0.25% by mass of vitamin $B_2$, 0.01–0.5% by mass of vitamin $B_6$, 0.001–0.01% by mass of vitamin $B_{12}$, 0.1–2% by mass of nicotinamide, 0.01–0.5% by mass of vitamin A, 0.0015–0.015% by mass of vitamin D, 0.1–5% by mass of vitamin C, 0.01–0.1% by mass of folic acid, 0.1–0.5% by mass of pantothenic acid, 0.01–7% by mass of vitamin E and 0.001–0.01% by mass of vitamin H.

The tablets according to the invention may contain besides the macro- and trace elements and vitamins also flavouring and aroma agents such as orange, lemon or pineapple aroma, lubricating agents such as polyethylene glycols, silicone oils, stearates or adipic acid, agents enhancing absorption such as tartaric acid and glycine, further any other additive usual in the manufacture of effervescent tablets.

The main advantages of the invention are as follows:

a) The tablets are chemically stable, can be readily compressed and have excellent physical properties.

b) The tablets and granules contain the active agents, that is the macro- and trace elements as well as the vitamins, in homogeneous distribution.

c) The tablets give after dissolving in water a clear beverage of agreeable flavour, without any sediment.

d) The presence of mannitol renders possible the use of malic acid as acidic sparkling component in a relatively high amount whereby the agreeable antioxidant, flavour-improving and optimal pH-setting effects of this acid can be enforced.

e) By using the mannitol effervescent tablets of low calory content and rich in macro- and trace elements and vitamins can be prepared which can be consumed also by diabetic persons.

f) In the known effervescent tablets containing vitamins and mineral agents the trace elements are used in crystal-water-free form or in a form containing only a small amount of crystal water. On the other hand, the invention renders possible the use of substances of high crystal-water content, which per se are only badly compressible or cannot be compressed at all, are the most stable modifications of the inorganic compounds and thereby can be prepared or procured at a lower price and in high purity.

g) By the common use of mannitol, malic acid and aspartame the homogeneous distribution of the macro- and trace elements and vitamins can be realized even when their amount is very low in relation to the mass of the ready tablet. The homogeneous distribution of vitamins is ensured without disadvantageously influencing the properties of these sensitive compounds during the technological procedures.

h) The invention renders possible to prepare effervescent tablets containing incompatible active agents such as vitamins as well as macro- and trace elements.

i) During the manufacture of the tablets the macro- and trace elements form complexes with the mannitol, whereby the chemical stability of the tablet as well as the absorption and biological utilization of the active agents become more favourable.

j) The invention renders possible the preparation of tablets by using sparkling components (potassium hydrogen carbonate and malic acid) and inorganic compounds with high crystal-water content (macro- and trace element sources) which, owing to their unfavourable properties, could not be previously used in the manufacture of effervescent tablets. Besides, the thus-obtained effervescent tablets have high breaking strength and give a clear solution with a short sparkling time.

The invention is further elucidated by the aid of the following non-limiting examples.

EXAMPLE 1

The granules ready for pressing are composed of four granules and a so-called outer phase.

| Granule I | |
|---|---|
| Vitamin $B_1$ | 7.29 g |
| Vitamin $B_2$ | 7.50 g |
| Vitamin $B_6$ | 10.94 g |
| Ca-pantothenate | 38.215 g |
| Nicotinamide | 85.00 g |
| Mannitol | 500.00 g |

After sieving the materials are homogenized, kneaded with ethanol, granulated, then the wet granules are dried and re-granulated.

| Granule II | |
|---|---|
| Iron(II)-sulphate heptahydrate | 99.55 g |
| Malic acid | 1500.00 g |
| Mannitol | 1500.00 g |

After sieving the materials are homogenized, kneaded with distilled water, granulated, dried, then re-granulated and post-dried.

| Granule III | |
|---|---|
| Potassium hydrogen carbonate | 3800.00 g |
| Mannitol | 3800.00 g |

After sieving and homogenizing the mass is kneaded with a mixture of water and ethanol, then after drying it is re-granulated.

| Granule IV | |
|---|---|
| Mannitol | 3925.00 g |
| Magnesium sulphate heptahydrate | 1571.50 g |
| Glycine | 150.00 g |
| Succinic acid | 250.00 g |
| Mannitol | 75.00 g |
| Selenious acid | 0.1635 g |
| Ammonium heptamolybdenate tetrahydrate | 0.690 g |
| Manganese(II)-sulphate monohydrate | 15.38 g |
| Copper(II)-sulphate pentahydrate | 29.47 g |
| Zinc sulphate heptahydrate | 219.95 g |

After grinding, homogenizing and kneading the mass is granulated with distilled water, then it is dried, re-granulated and post-dried.

| Materials of the outer phase | |
|---|---|
| Vitamine C | 300.00 g |
| Malic acid | 3000.00 g |
| Polyethylene glycol | 710.00 g |
| Aspartame | 200.00 g |
| Lemon aroma | 1000.00 g |

After sieving and grinding the materials of the outer phase are homogenized. The thus-obtained pre-homogenizate is admixed with the granules I, II, III and IV and the thus-obtained mixture is homogenized. From the granules obtained in this way about 5000 tablets with a diameter of 32 mm and an average weight of 4.5 g are compressed.

EXAMPLE 2

One proceeds in the same way as described in Example 1 with the difference that the vitamins are supplemented with vitamin E and the amounts of the components are changed in the following way:

| Name of the component | Amount (g) |
|---|---|
| Iron(II)-sulphate ($FeSO_4 \cdot 7H_2O$) | 99.56 |
| Zinc(II)-sulphate ($ZnSO_4 \cdot 7H_2O$) | 109.97 |
| Copper(II)-sulphate ($CuSO_4 \cdot 5H_2O$) | 14.74 |
| Manganese(II)-sulphate ($MnSO_4 \cdot H_2O$) | 7.69 |
| Ammonium molybdenate [$(NH_4)_6Mo_7O_{24} \cdot 4H_2O$] | 0.276 |
| Selenious acid ($H_2SeO_3$) | 0.082 |
| Magnesium sulphate ($MgSO_4 \cdot 7H_2O$) | 608.34 |
| Vitamin $B_1$ (thiamine.HC1) | 3 |
| Vitamin $B_2$ (riboflavine) | 3.5 |
| Vitamin $B_6$ (pyridoxine.HCl) | 4 |
| Nicotinamide | 40 |
| Vitamin C [L-(+)-ascorbic acid] | 175 |
| Phantothenic acid (Ca-pantothenate) | 15 |
| Vitamin E (DL-α-tocoferol) | 25 |
| Succinic acid | 100 |
| Glycine | 75 |
| Malic acid | 2750 |
| Potassium hydrogen carbonate ($KHCO_3$) | 2300 |
| Mannitol | 6500 |
| Aspartame | 200 |
| Pineapple aroma | 1000 |
| Polyethylene glycol | 750 |

From the granules ready for pressing about 5000 tablets having a diameter of 25 mm and an average weight of 3 g are stamped.

EXAMPLE 3

One proceeds as described in Example 1 with the difference that the microelements are supplemented with chromium and the vitamins with vitamins $B_{12}$, A, D and H and folic acid, furthermore the amounts of the components are changed in the following way:

| Name of the component | Amount (g) |
|---|---|
| Iron(II)-sulphate ($FeSO_4 \cdot 7H_2O$) | 373.35 |
| Zinc(II)-sulphate ($ZnSO_4 \cdot 7H_2O$) | 329.97 |
| Copper(II)-sulphate ($CuSO_4 \cdot 5H_2O$) | 39.29 |
| Manganese(II)-sulphate ($MnSO_4 \cdot H_2O$) | 38.46 |
| Ammonium molybdenate [$(NH_4)_6Mo_7O_{24} \cdot 4H_2O$] | 1.38 |
| Selenious acid ($H_2SeO_3$) | 0.2 |
| Chromium(III)-chloride ($CrCl_3 \cdot 6H_2O$) | 1.28 |
| Magnesium sulphate ($MgSO_4 \cdot 7H_2O$) | 5069.5 |
| Vitamin $B_1$ (thiamine.HCl) | 7.5 |

-continued

| Name of the component | Amount (g) |
|---|---|
| Vitamin $B_2$ (riboflavine) | 8.5 |
| Vitamin $B_6$ (pyridoxine.HCl) | 10 |
| Vitamin $B_{12}$ (cyanocobalamin) | 0.01 |
| Nicotinamide | 95 |
| Vitamin A | 5 |
| Vitamin D | 0.05 |
| Vitamin C [L-(+)-ascorbic acid] | 450 |
| Folic acid | 1 |
| Pantothenic acid (Ca-pantothenate) | 35 |
| Vitamin E (DL-α-tocoferol) | 50 |
| Vitamin H (biotine) | 325 |
| Succinic acid | 300 |
| Glycine | 180 |
| Malic acid | 6000 |
| Potassium hydrogen carbonate ($KHCO_3$) | 5000 |
| Mannitol | 11500 |
| Aspartame | 300 |
| Orange aroma | 1500 |
| Polyethylene glycol | 2000 |

From the granules ready for compressing about 5000 tablets having a diameter of 35 mm and a weight of 6.6 g are compressed.

EXAMPLE 4

One proceeds as described in Example 3 with the difference that the amount of malic acid is changed to 3500 g, that of potassium hydrogen carbonate to 2800 g, that of mannitol to 16,000 g and that of aspartame to 150 g. From the granules ready for compressing about 5000 tablets having a diameter of 32 mm and an average weight of 6.6 g are compressed.

EXAMPLE 5

One proceeds as described in Example 3 with the difference that the amount of malic acid is changed to 10,000 g, that of potassium hydrogen carbonate to 9000 g, that of mannitol to 8000 g and that of aspartame to 800 g. From the granules ready for compressing about 5000 tablets having a diameter of 32 mm and an average weight of 7.7 g are compressed.

What we claim is:

1. Effervescent tablets and granules comprising 20–50% by mass of mannitol as shell material, 8–25% by mass of potassium hydrogen carbonate as basic sparkling component, 9–27% by mass of malic acid as acidic sparkling component, 0.4–2.2% by mass of aspartame as sweetening agent, magnesium, zinc, iron(II), copper(II), manganese(II) and chromium(III) cations, molybdenum(VI) and selenium (IV) anions as macro and trace elements, and optionally vitamins as active agents, and flavoring and lubricating additives used in the manufacture of effervescent tablets in an amount necessary to supplement the mass of the components to 100%.

2. Effervescent tablets or granules as defined in claim 1, which comprise 30–40% by mass of mannitol, 14–18% by mass of potassium hydrogen carbonate, 15–21% by mass of malic acid, and 0.6–1.5% by mass of aspartame.

3. A process for preparing effervescent tablets or granules comprising the steps of homogenizing 20–50% by mass of mannitol, 8–25% by mass of potassium hydrogen carbonate, 9–24 by mass of malic acid, and 0.4–2.2% by mass of aspartame together with the magnesium, zinc, iron(II), copper(II), manganese(II) and chromium(III) cations, molybdenum(VI) and selenium(IV) anions and vitamins to be introduced and optionally together with flavoring, lubricating and additives used in the manufacture of effervescent tablets, then granulating the thus-obtained homogenizate to granules ready for compressing, and finally compressing tablets or granules of the desired size and strength.

4. Effervescent tablets or granules as defined in claim 1, wherein the iron ions are contained in the form of ferrosulphate heptahydrate, the zinc ions in the form of zinc sulphate heptahydrate, the copper ions in the form of copper sulphate pentahydrate, the manganese ions in the form of manganese sulphate monohydrate, the molybdenum ions in the form of ammonium heptamolybdenate tetrahydrate, the selenium ions in the form of selenious acid, the magnesium ions in the form of magnesium sulphate heptahydrate, and the chromium ions in the form of chromium(III) chloride hexahydrate.

5. Effervescent tablets or granules as claimed in claim 1, wherein the vitamins are present in the following amounts related to the mass of the composition: 0.01–0.5% by mass of vitamin $B_1$, 0.01–0.25% by mass of vitamin $B_2$, 0.01–0.5% by mass of vitamin $B_6$, 0.001–0.01% by mass of vitamin $B_{12}$, 0.1–2% by mass of nicotinamide, 0.01–0.5% by mass of vitamin A, 0.0015–0.015% by mass of vitamin D, 0.1–5% by mass of vitamin C, 0.01–0.1% by mass of folic acid, 0.1–0.5% by mass of pantothenic acid, 0.01–7% by mass of vitamin E and 0.001–0.01% by mass of vitamin H.

6. A process as defined in claim 3, in which 30–40% by mass of mannitol, 14–18% by mass of potassium hydrogen carbonate, 15–21% by mass of malic acid, and 0.6–1.5% by mass of aspartame are homogenized with the other components of the tablet.

* * * * *

UNITED STATES PATENT AND TRADEMARK OFFICE
CERTIFICATE OF CORRECTION

PATENT NO.: 5,707,654

DATED: January 13, 1998

INVENTOR(S): BERES et al.

It is certified that error appears in the above-identified patent and that said Letters Patent is hereby corrected as shown below:

Column 8, claim 3, line 13, after "9-24" insert --%--.

Signed and Sealed this

Third Day of March, 1998

Attest:

BRUCE LEHMAN

*Attesting Officer*  *Commissioner of Patents and Trademarks*